United States Patent [19]
Racenet et al.

[11] Patent Number: 5,713,911
[45] Date of Patent: Feb. 3, 1998

[54] SURGICAL CLIP

[75] Inventors: David C. Racenet, Southbury; John W. Beardsley, Hamden, both of Conn.

[73] Assignee: United States Surgical Corporation, Norwalk, Conn.

[21] Appl. No.: 756,962

[22] Filed: Oct. 3, 1996

[51] Int. Cl.[6] ................................. A61B 17/08
[52] U.S. Cl. ..................... 606/157; 606/158; 606/151
[58] Field of Search ............................. 606/151, 157, 606/158, 142, 143; 24/546, 545; 227/902

[56] References Cited

U.S. PATENT DOCUMENTS

| | | |
|---|---|---|
| 3,006,344 | 10/1961 | Vogelfanger . |
| 3,175,556 | 3/1965 | Wood et al. . |
| 3,363,628 | 1/1968 | Wood . |
| 3,378,010 | 4/1968 | Codling ........................... 128/325 |
| 3,867,944 | 2/1975 | Samuels . |
| 3,874,042 | 4/1975 | Eddleman et al. . |
| 4,064,881 | 12/1977 | Meredith . |
| 4,146,130 | 3/1979 | Samuels et al. . |
| 4,188,953 | 2/1980 | Klieman et al. . |
| 4,278,091 | 7/1981 | Borzone . |
| 4,346,869 | 8/1982 | MacNeill . |
| 4,394,864 | 7/1983 | Sandhaus . |
| 4,407,286 | 10/1983 | Noiles et al. . |
| 4,412,539 | 11/1983 | Jarvik . |
| 4,414,721 | 11/1983 | Hufnagel . |
| 4,434,795 | 3/1984 | Mericle ........................... 128/303 R |
| 4,449,530 | 5/1984 | Bendel et al. . |
| 4,487,205 | 12/1984 | Di Giovanni et al. . |
| 4,489,875 | 12/1984 | Crawford et al. . |
| 4,519,392 | 5/1985 | Lingua . |
| 4,531,522 | 7/1985 | Bedi et al. . |
| 4,570,623 | 2/1986 | Ellison et al. . |
| 4,590,937 | 5/1986 | Deniega ........................... 128/325 |
| 4,624,254 | 11/1986 | McGarry et al. . |
| 4,702,247 | 10/1987 | Blake, III et al. ................... 128/325 |
| 4,796,627 | 1/1989 | Tucker . |
| 4,799,481 | 1/1989 | Transue et al. . |
| 4,844,066 | 7/1989 | Stein . |
| 4,934,364 | 6/1990 | Green ................................ 606/143 |
| 4,971,198 | 11/1990 | Mericle . |
| 4,976,722 | 12/1990 | Failla ................................ 606/157 |
| 4,979,950 | 12/1990 | Transue et al. . |
| 5,171,250 | 12/1992 | Yoon . |
| 5,171,252 | 12/1992 | Friedland . |
| 5,171,253 | 12/1992 | Klieman . |
| 5,201,746 | 4/1993 | Shichman ............................ 606/151 |
| 5,425,740 | 6/1995 | Hutchinson, Jr. . |
| 5,509,920 | 4/1996 | Phillips et al. ...................... 606/157 |

FOREIGN PATENT DOCUMENTS

| | | | |
|---|---|---|---|
| 285776A | 10/1988 | European Pat. Off. | ............ 17/12 |
| 853499 | 10/1952 | Germany . | |
| 8522122 | 10/1985 | Germany . | |

*Primary Examiner*—Michael Buiz
*Assistant Examiner*—Tina T. D. Pham

[57] ABSTRACT

A surgical clip with advantageous closure characteristics is disclosed which includes a bail portion having first and second back portions joined at an apex, and rectilinear leg portions extending from the back portions. The apex is preferably characterized by an angle of no more than about 100°. Preferably the outer surface of at least one back portion includes a compression ridge to concentrate the compression force applied by the jaws of the applying instrument to a preselected region of the clip. The legs retain their parallelism while the clip is being closed. Additional features include interlocking ridges and/or projections on one of the legs which engage corresponding recesses on the other leg to enhance clip retention on tissue and to help minimize twisting and/or scissoring of the clip legs during closure.

20 Claims, 7 Drawing Sheets

SURGICAL CLIP

BACKGROUND

1. Technical Field

This disclosure relates generally to surgical clips and, more particularly, to a surgical clip having advantageous closure characteristics.

2. Background of Related Art

Ligation or occlusion of veins, arteries or blood vessels has been a necessary part of surgical procedures for many years. Typically, a severed blood vessel requires closure on both sides of a severance site before actual cutting takes place. In the past, surgeons used thread or suture material to tie a blood vessel prior to severing the vessel. This procedure was often time-consuming and requires dexterity on the part of the surgeon to properly close the vessel. In many instances, the assistance of a nurse of attending surgeon was necessary to perform this procedure.

The advent of surgical clips and clip appliers has greatly enhanced the art of vessel occlusion. Surgical clips are now commonly used for vessel ligation and occlusion. Examples of surgical hemostatic clips are described in U.S. Pat. Nos. 5,171,253; 5,171,252; 5,100,420; 5,084,057; 4,971,198; 4,844,066; 4,799,481; 4,702,247; 4,414,721; 4,188,953; 4,146,130; 3,867,944 and 3,363,628.

Many factors impact upon the design of a surgical hemostatic clip. For example, it is generally important that the clip does not slip or become dislodged from a blood vessel after it has been applied, at least during an initial period of time.

Surgical hemostatic clips should fully and completely close about the vein, artery, or blood vessel to which they are applied without undesirable gaps to insure that the blood flow through the lumen of the vessel is completely occluded.

Also, clip legs should not shift laterally with respect to each other during closure. In the industry, legs that have shifted a relatively small amount are said to have "twisted". If the misalignment is relatively large, the industry generally refers to such clip as having "scissored". Clip legs can also shift longitudinally with respect to each other. Scissoring or twisting of a clip may result in damage to tissue and enlargement of the gap between the clip legs while longitudinal misalignment generally affects only the gap.

Generally, surgical hemostatic clips are U-shaped or V-shaped in configuration and define a pair of legs joined at one end by an apex or crown and spaced apart at the opposed ends to define an opening therebetween. Clips often have a bail portion, which is the arcuate or V-shaped back portion, and substantially parallel legs extending from the bail portion. The inside surfaces of the clip legs may be constructed in a manner to improve the occluding functions of the clip as well as to restrict longitudinal and transverse dislocation of the clip after it has been applied to the target blood vessel. An example of a clip having surface features is described in U.S. Pat. No. 4,976,722 which issued to Failla.

Another factor in the design of surgical hemostatic clips relates to its storage and advancement through a clip applying instrument designed to apply multiple clips. In certain commercially available clip appliers, the surgical clips are stored in a linear array extending longitudinally along the instrument with the legs of one clip contacting the bail portion of the preceding clip. As each clip is applied, the entire row of clips is advanced such that the distal-most clip is positioned within the jaws or in the on-deck position. Thus, the shape, size and overall geometry of a surgical clip can affect its movement through the clip applying apparatus.

Figure 3:
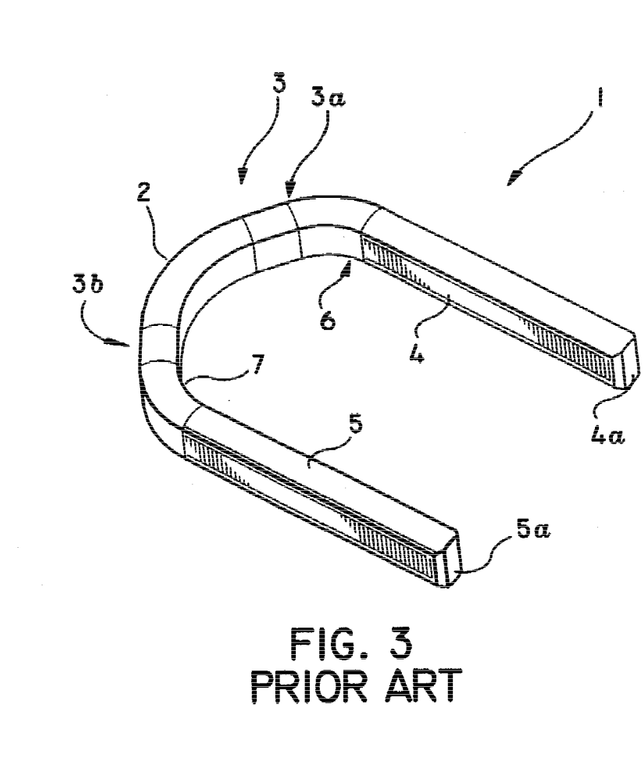
FIG. 3 is a perspective view of a prior art surgical clip.
Figure 4:
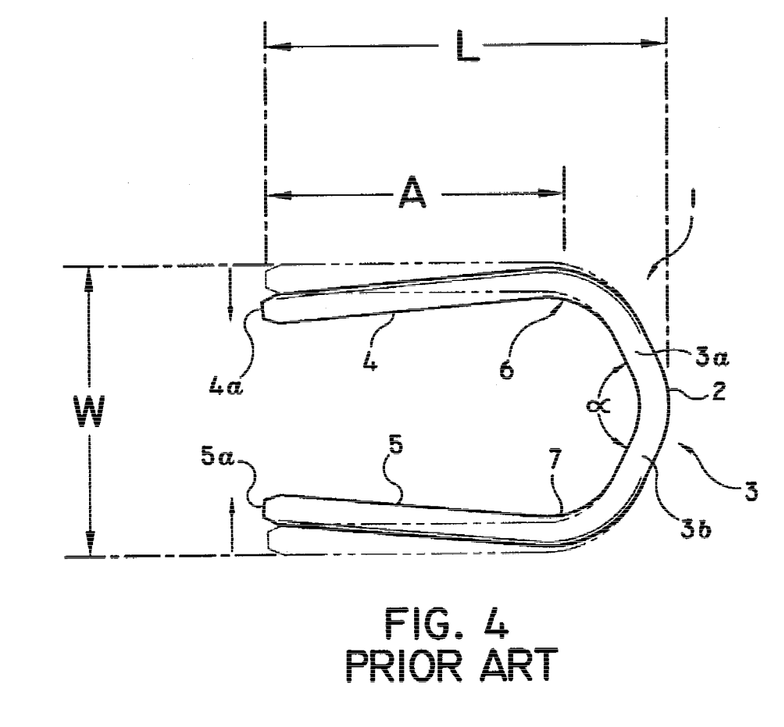
FIG. 4 is a top plan view of the prior art surgical clip of FIG. 3 during closure of the clip.
Figure 4A:
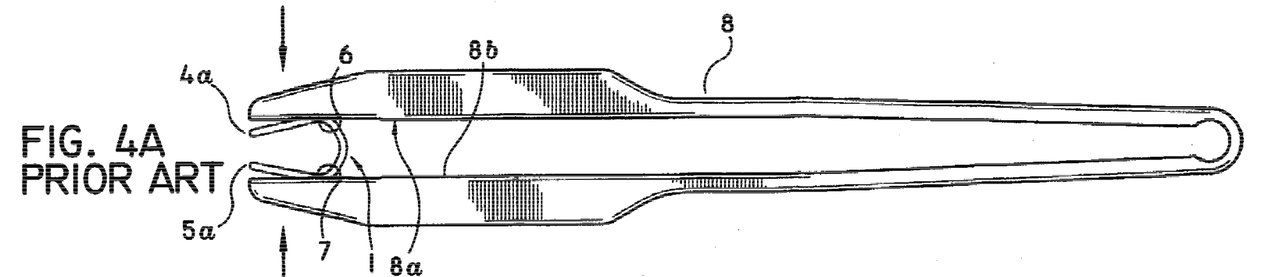
FIG. 4A is a top plan view of a prior art clip applier jaw holding and closing the prior art surgical clip of FIG. 3.
Figure 4B:
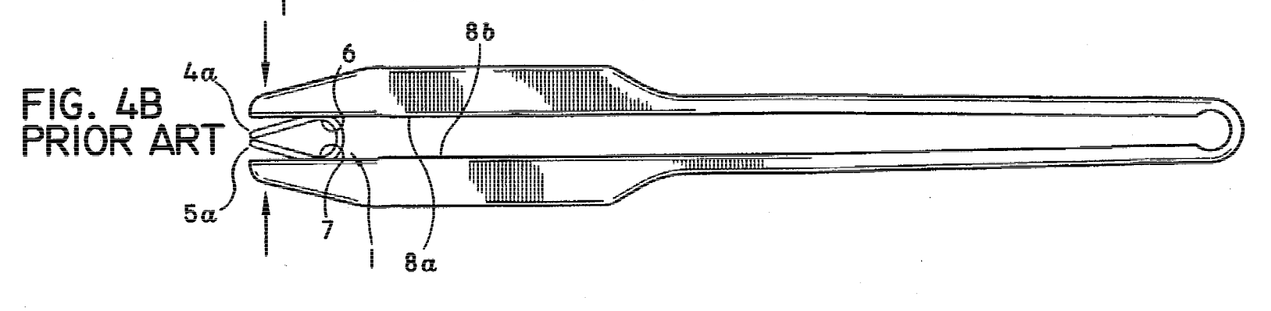
FIG. 4B is a view similar to FIG. 4A showing further closure of the prior art surgical clip.

Referring now to FIGS. 3, 4, 4A and 4B, a prior art type surgical clip is illustrated. Prior art clip 1 includes a bail portion 3 having angled back portions 3a and 3b connected to each other at apex 2. Apex 2 is characterized by angle "a". The bail portion is demarcated by bend regions 6 and 7, wherein back portions 3a and 3b are connected to legs 4 and 5. Legs 4 and 5 are rectilinear and initially parallel to each other. They terminate at distal ends 4a and 5a, respectively. Referring to FIG. 4, clip 1 has an overall length L defined by the distance between the distal ends 4a and 5a, and the outer edge of apex 2. Clip 1 has a width W defined by the distance between the outer surfaces of the legs 4 and 5. Legs 4 and 5 have a length "A" defined by the distance between the distal ends 4a and 5a and the bend regions 6 and 7.

The prior art clip illustrated herein is characterized by a width (W) to total length (L) ratio (W/L) of about 0.72. The ratio of leg length (A) to total length (L) (A/L) is abut 0.74. Angle "a" is about 125°. Prior art clip 1 has good characteristics for movement through a prior art clip applier and satisfactory closure characteristics. Nonetheless, room for development of an optimized surgical clip exists

SUMMARY OF THE INVENTION

A surgical clip is provided herein which has improved closure characteristics while retaining good facility to move through a clip applier track without jamming. The surgical clip includes (a) a bail portion having first and second linear, and preferably arcuate, back portions joined to each other at an apex, wherein each of the first and second back portions has an exterior surface and an interior surface; and (b) first and second rectilinear legs, each leg having a distal free end and an interior tissue contacting surface and an exterior surface for receiving a compressive force, each leg being joined to a respective one of the first and second back portions and moveable in response to an externally applied compressive force from an initial spaced apart, open configuration to a closed configuration, wherein the first and second legs are in close proximity to each other. The legs are preferably initially substantially parallel to each other and remain substantially parallel to each other when moved from the open configuration to the closed configuration. Preferably, the exterior surface of the second back portion includes an elongated ridge extending along the linear orientation of the second back portion.

Dimensionally, the ratio of the overall clip width to the overall clip length preferably ranges from about 0.68 to abut 0.64, and the ratio of the length of the legs to the total length of the clip ranges from about 0.36 to about 0.33, the legs being of preferably equal length. The apex is preferably characterized by an angle of less than about 100°.

The interior surface of the first back portion preferably includes an elongated ridge extending along the linear orientation of the first back portion, and the interior surface of the second back portion preferably includes a corresponding recess for receiving the elongated ridge of the first back portion upon movement of the clip legs from the open to the closed position. Also, the interior surface of the second clip leg preferably includes an interlock protrusion and the interior surface of the first leg includes a corresponding recess for receiving the interlock protrusion of the second leg upon movement of the first and second legs from the open position to the closed position.

BRIEF DESCRIPTION OF THE DRAWINGS

Various embodiments are described herein below with reference to the drawings, wherein.

DETAILED DESCRIPTION OF PREFERRED EMBODIMENTS

The disclosed embodiments of the advantageous surgical clip are designed to be applied to body tissue by a surgical clip applying apparatus. A surgical clip applying apparatus generally has a pair of jaws to position the clip relative to tissue and to deform or close the clip about tissue, usually by bending the clip near its apex such that the legs of the clip close about the tissue, such as, for example, a blood vessel. Suitable surgical instruments for use in the application of the disclosed surgical clips embodiments are described in U.S. Pat. No. 4,509,518 to McGarry et al., and U.S. Pat. Nos. 5,084,057 and 5,100,420 to Green et al., the disclosures of which are herein incorporated by reference.

Figure 1:
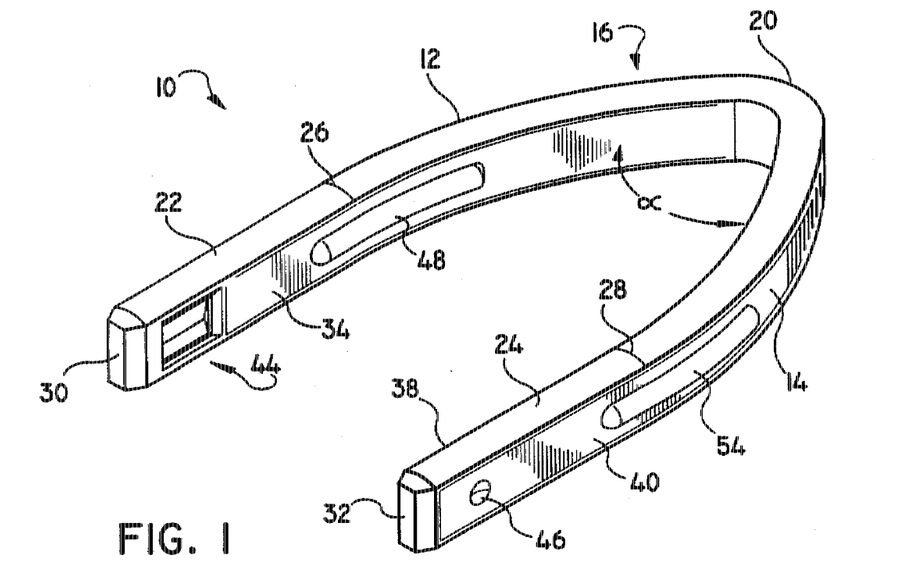
FIG. 1 is a perspective view of one embodiment of an advantageous surgical clip.
Figure 2:
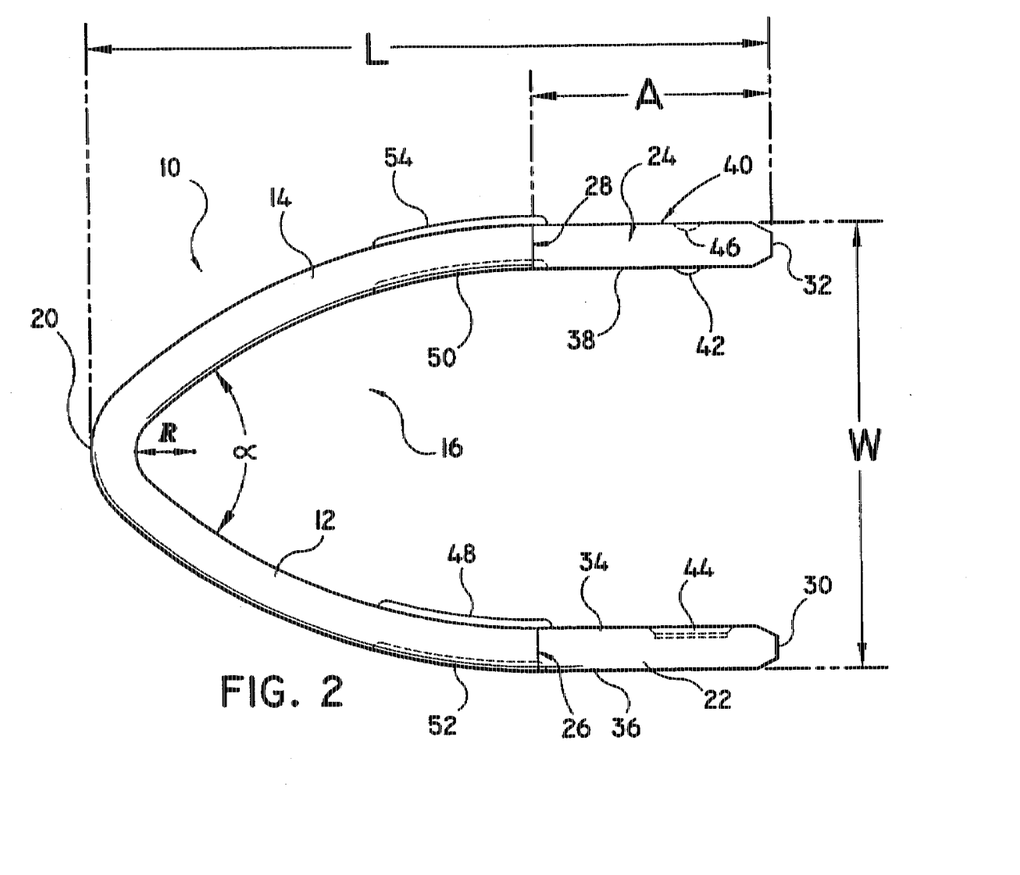
FIG. 2 is a top plan view of the embodiment of FIG. 1.

Referring to FIGS. 1 and 2, the advantageous surgical clip 10 has a bail portion 16 with first and second gently curved back portions 12 and 14 which meet at a single, sharply defined bend or apex 20. Preferably, the angle "a" to be formed at apex 20 is no more than about 100°. First and second substantially straight legs 22 and 24 extend from regions 26 and 28 which demarcate the ends of curved back portions 12 and 14. The bail portion 16 of the clip 10 terminates at regions 26 and 28 where curved back portions 12 and 14 meet straight legs 22 and 24, respectively. First and second legs 22 and 24 are preferably parallel to one another and terminate in free ends 30 and 32, respectively.

The inner surfaces of the back portions 12 and 14 and associated legs 22 and 24 define tissue contacting surfaces 34 and 38, respectively, between which tissue is clamped during application of surgical clip 10 to tissue. The outer surfaces of the back portions 12 and 14 and associated legs 22 and 24 define jaw contact surfaces 36 and 40 for receiving the compression force from the jaws of the applying apparatus. Clip 10 is dimensioned such that the ratio of width W to total length L (i.e., the ratio W/L) ranges from about 0.68 to about 0.64, and the ratio of leg length A to total length L (i.e., the ratio A/L) ranges from about 0.36 to about 0.33, wherein the width W is the distance between the outer surfaces of the legs, the total clip length L is the distance between the outer edge of the apex 20 and the distal ends 30, 32 of the legs, and the leg length A is the distance between the juncture regions 26, 28 and the distal ends 30, 32 of the legs. Legs 22 and 24 are preferably of equal length.

The curvature of the clip at apex 20 is the most pronounced curvature throughout the entire clip. Thus, apex 20 has a radius of curvature R wherein R is about, four percent (4%) of the length L of the clip 10. The arcuate back portions 12, 14 preferably include no radiused portion having a radius of curvature of less than about six times the radius of curvature (R) of the apex.

Surgical clip 10 includes an interlock protrusion 42 projecting from tissue contacting surface 38 on the second leg 24 and an interlock recess 44 formed in tissue contacting surface 34 on first leg 22 which interlock upon closure to aid in maintaining tips 30, 32 in proper alignment, thereby optimizing clip retention on tissue and further minimizing the potential for twist. A dimple 46 is generally formed in jaw contacting surface 40 during formation of interlock protrusion 42.

Figure 2A:
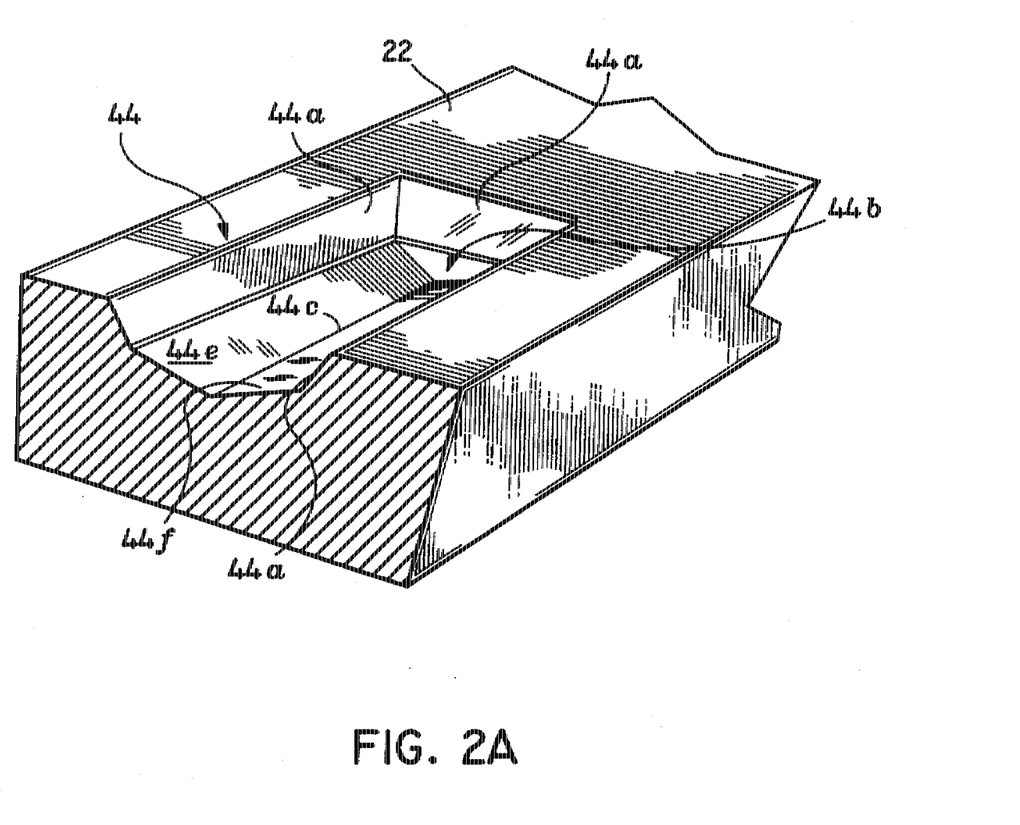
FIG. 2A is a detailed sectional view of a clip leg.

Referring to FIG. 2A, interlock protrusion 42 can be substantially circular whereas the recess 44 adopted to receive protrusion 42 is preferably rectangular in shape, and larger than protrusion 42. Recess 44 preferably possesses beveled upper sides 44a and a synclined base 44b having an elongated line 44c oriented along the length of leg 22 defined by the intersection of angled planar surfaces 44f and 44e.

Surgical clip 10 is designed to exhibit improved closure characteristics, e.g., optimal clip retention on tissue and minimum twist during formation. Additionally, surgical clip 10 includes structure to minimize the amount of "gap" or distance between the tissue contacting surfaces 34 and 38 upon closure, thereby enhancing alignment of arms 12 and 14. Surgical clip 10 further includes an elongated alignment rib 48 projecting from tissue contacting surface 34 and a contacting surface 38 which is adapted to receive rib 48. An elongate depression 52 is formed in jaw contacting surface 36 upon formation of alignment rib 48. Similarly, a projection or local compression rib 54 results from the formation of alignment depression 50. Local compression rib 54 advantageously assists in distributing the compressive force applied by the jaws, concentrating the force locally at the area most likely to exhibit meaningful gap, thereby locally compressing the area to achieve minimal gap and enhance clip retention on tissue.

Figure 5:
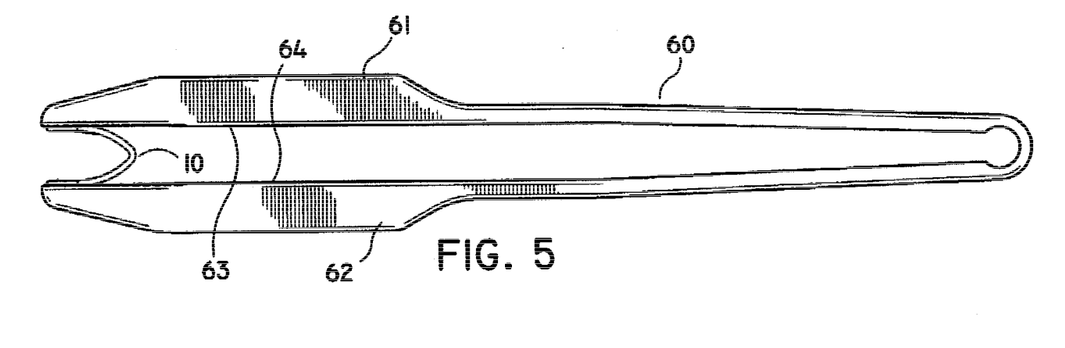
FIG. 5 is a top plan view of a prior art clip applier jaw holding the surgical clip of FIG. 1 prior to closure.

Referring now to FIGS. 5 which shows placement of clip 10 within the apparatus jaws prior to the initiation of closure, jaw structure 60 includes individual jaws 61 and 62 having opposing clip contacting surfaces 63 and 64, respectively. Clip 10 is shown positioned between the jaws 61 and 62 such that the outer surfaces 36, 40 of the parallel legs 22 and 24 are in contacting relationship with clip contacting surfaces 63 and 64.

Figure 6:
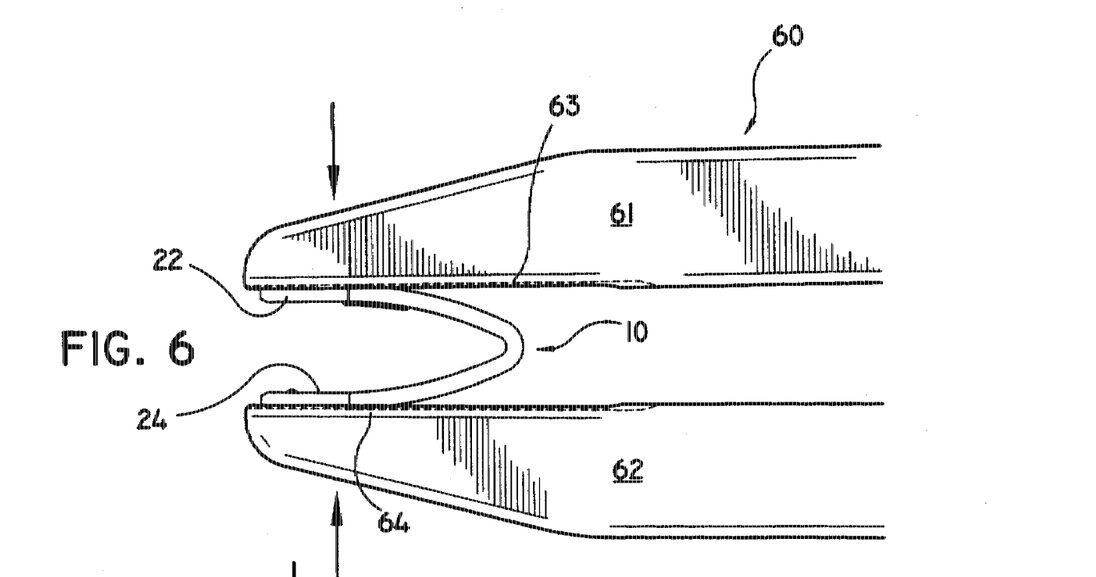
FIG. 6 is an enlarged view of the distal end of the prior art jaw of FIG. 5 showing initial closure of the surgical clip.
Figures 7, 8:
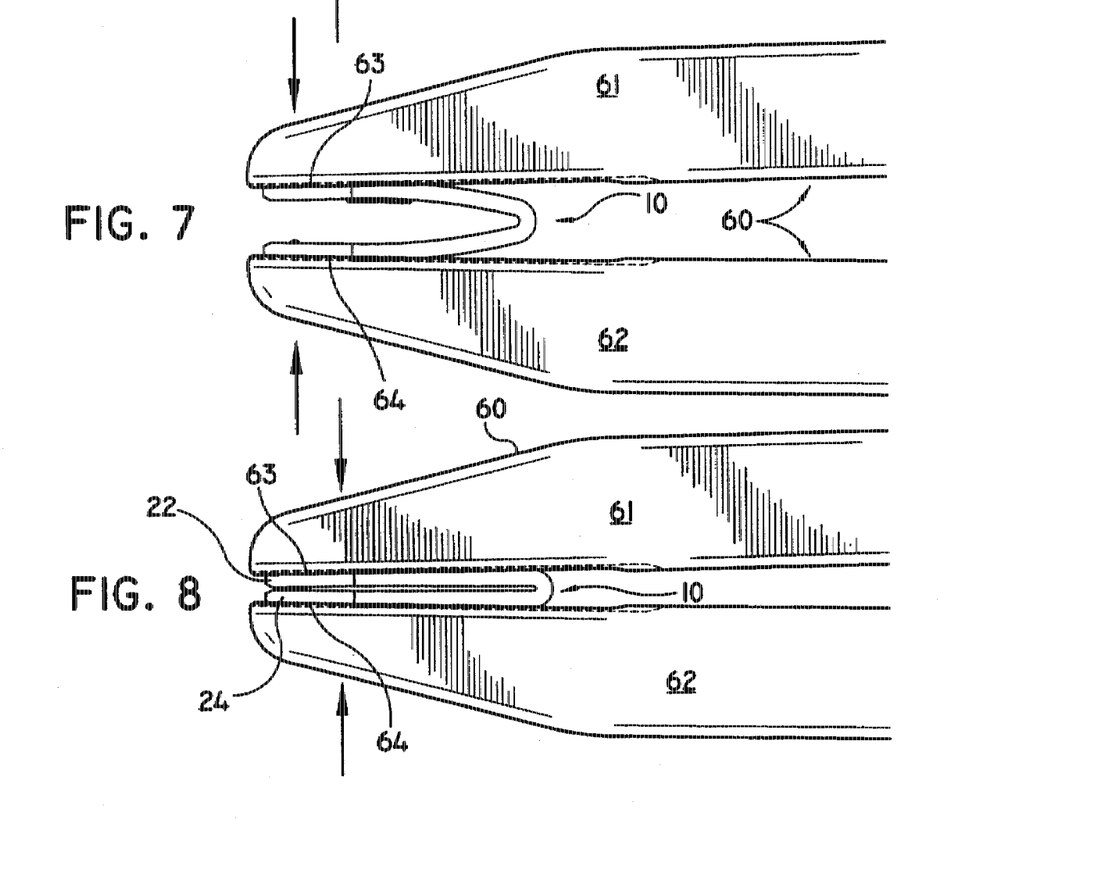
FIG. 7 is a view similar to FIG. 6 showing partial closure of the surgical clip.
FIG. 8 is a view similar to FIG. 7 showing complete closure of the surgical clip of FIG. 1.

Referring now to FIGS. 6, 7, and 8, sequential views of clip closure are illustrated. Legs 22 and 24 are closed by the jaws such that they remain parallel to each other and lock together, thereby minimizing the potential for significant lateral or longitudinal misalignment. The compression ridge 54 of the clip receives the compression force of the jaws and, in effect, advantageously concenetrates the compressive force onto the bail area of the clips in the vicinity of the juncture between the bail portion and the legs (i.e., regions 26 and 28).

Figure 9:
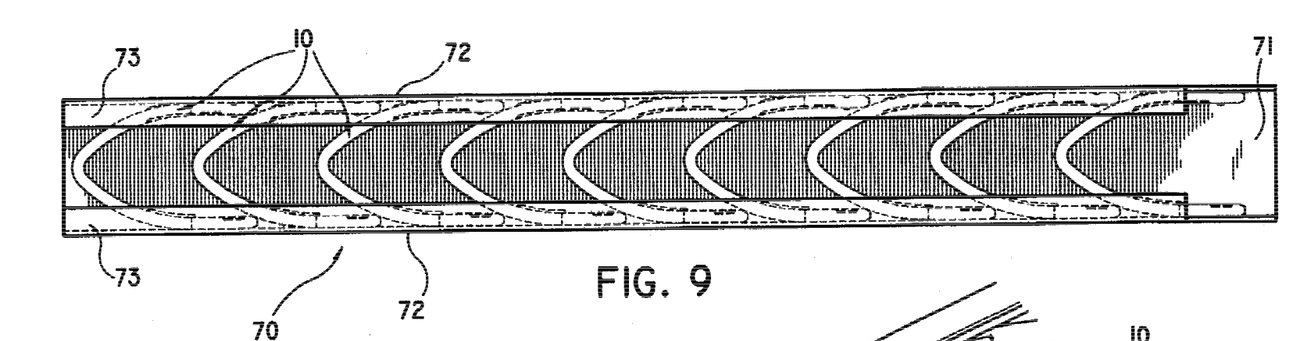
FIG. 9 is a top plan view of a plurality of surgical clips of FIG. 1 positioned in series array in a surgical clip magazine.
Figure 10:
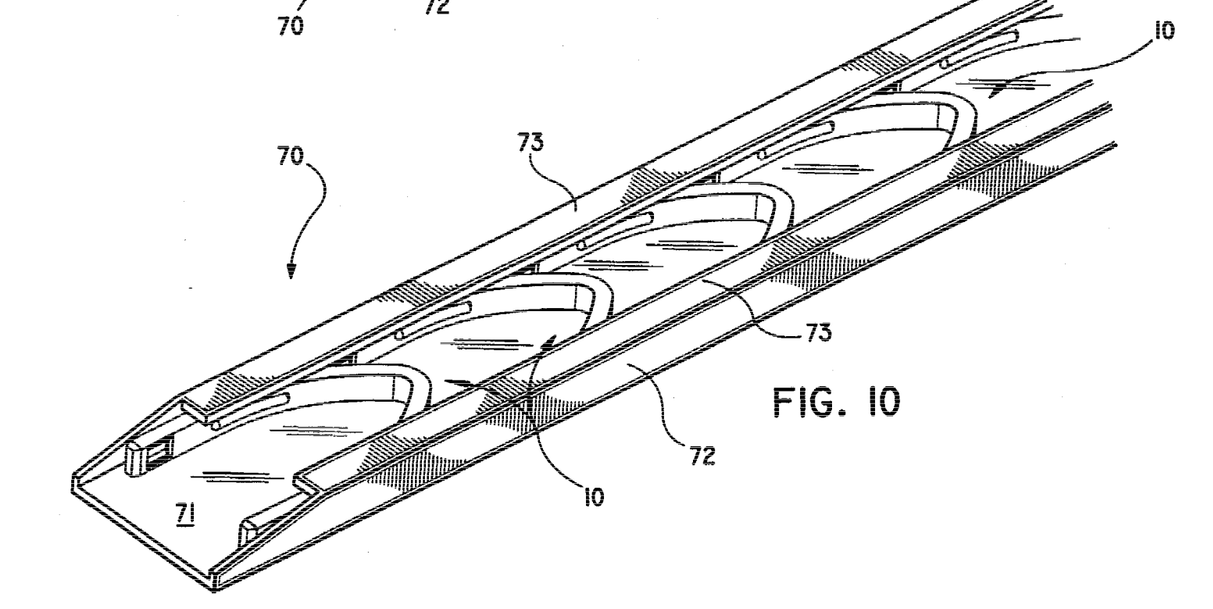
FIG. 10 is a perspective view of the surgical clip magazine containing a series of surgical clips of FIG. 1.

Referring now to FIGS. 9 and 10, a row of clips 10 is shown in clip storage and feeding track 70 having base 71, sides 72, and retainer walls 73. The clips 10 are stored in a linear array extending longitudinally through the clip applying instrument (not shown). The distal tips of the legs of one clip abut the bail portion of the preceding clip. The entire row of clips is advanced, thereby moving the most distal clip forward, ultimately into the jaws of the instrument for application to tissue.

Figure 11:
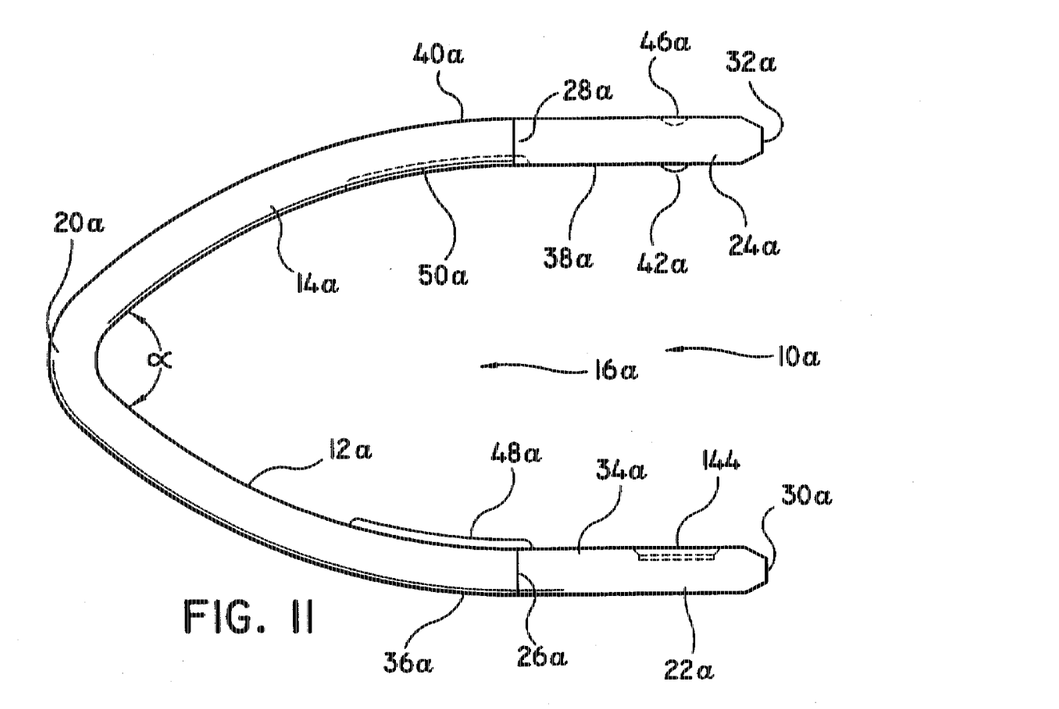
FIG. 11 is a top plan view of an alternate embodiment of an advantageous surgical clip.
Figure 12:
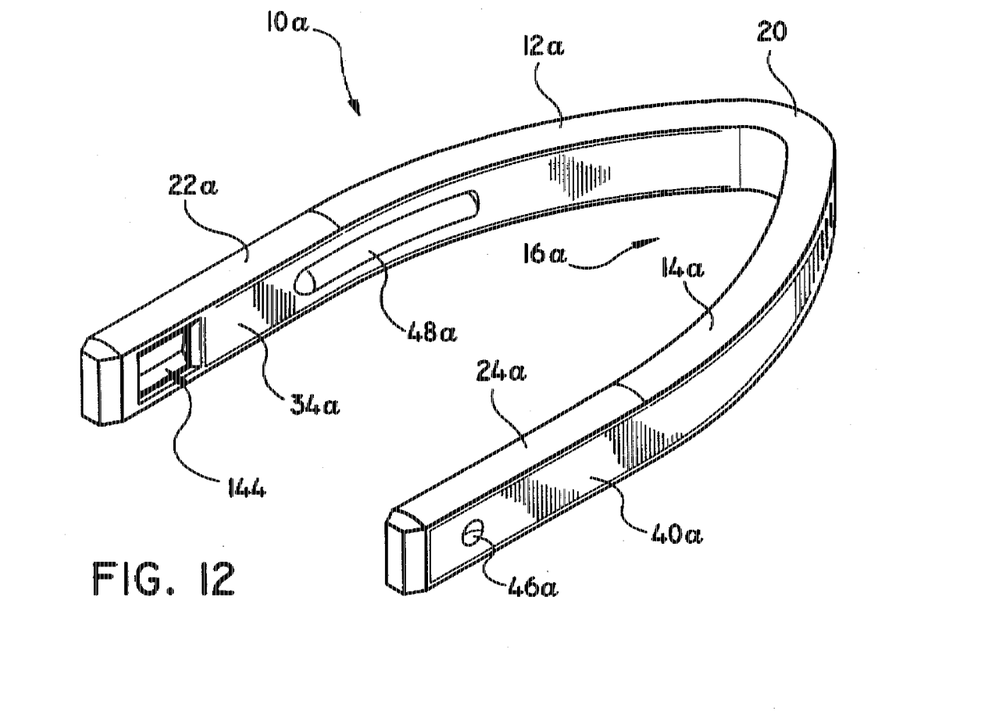
FIG. 12 is a perspective view of the alternate embodiment of FIG. 11.

Referring now to FIGS. 11 and 12, an alternative embodiment is depicted wherein clip 10a includes a bail portion 16a with first and second gently curved back portions 12a and 14a that meet at a single, sharply defined bend or apex 20a. First and second substantially straight legs 22a and 24a extend from regions 26a and 28a which demarcate the ends of curved back portions 12a and 14a. The bail portion 16a of the clip 10a terminates at regions 26a and 28a where curved back portions 12a and 14a meet straight legs 22a and 24a, respectively. First and second legs 22a and 24a are preferably parallel to one another and terminate in free ends 30a, 32a respectively.

The inner surfaces of the back portions 12a and 14a and associated legs 22a and 24a define tissue contacting surfaces 34a and 38a, respectively, between which tissue is clamped during application of surgical clip 10a thereto. The outer surfaces of the back portions 12a and 14a and associated legs 22a and 24a define jaw contact surfaces 36a and 40a which receive the compression force from the jaws of the applying apparatus. The length and width and angle dimensions of clip 10a are preferably similar to those of clip 10.

Surgical clip 10a includes an interlock protrusion 42a projecting from tissue contacting surface 38a and a corresponding interlock recess 144 formed in tissue contacting surface 34a. These features interlock upon clip closure to aid in maintaining tips 30a, 32a in proper alignment on tissue and to minimize twist. A dimple 46a is formed in jaw contacting surface 40a during formation of interlock protrusion 42a.

Like clip 10, alternate surgical clip 10a includes an elongated alignment rib 48a projecting from tissue contacting surface 34a and a corresponding alignment depression 50a formed in tissue contacting surface 38a. In contrast to clip 10, however, embodiment 10a has no equivalent of recess 52 or of compression ridge 54.

Clips 10 and 10a can be fabricated from any biocompatible material with properties suitable for the purposes described herein. Preferred materials for clip fabrication include stainless steel alloys and titanium, for example.

It will be understood that various modifications may be made to the embodiments disclosed herein. For example, the interlocking protrusion 42 and interlock recess 44 may be positioned on the alternate respective legs. Therefore the above description should not be construed as limiting, but merely as exemplifications of preferred embodiments. Those skilled in the art will envision other modifications within the scope and spirit of the claims appended hereto.

What is claimed is:

1. A surgical clip which comprises:
a) a bail portion having first and second linear back portions joined to each other at an apex, wherein each of the first and second back portions has an exterior surface and an interior surface;
b) first and second rectilinear legs, each leg having a distal free end and an interior tissue contacting surface and an exterior surface for receiving a compressive force, each leg being joined to a respective one of the first and second back portions and moveable in response to an externally applied compressive force from an initial spaced apart open configuration to a closed configuration, wherein the first and second legs are initially substantially parallel to each other and remain substantially parallel to each other during the process of moving from the open configuration to the closed configuration.

2. The surgical clip of claim 1, wherein the exterior surface of the second back portion includes an elongated ridge extending along the linear orientation thereof.

3. The surgical clip of claim 1, wherein the apex is characterized by an angle of no more than about 100°.

4. The surgical clip of claim 1, wherein the clip is characterized by a total length which is defined by the distance between the apex and the free ends of the first and second legs, and a width which is defined by the distance between the exterior surfaces of the first and second legs, and the ratio of the width to the length ranges from about 0.68 to about 0.64.

5. The surgical clip of claim 4, wherein the first and second legs are of equal length.

6. The surgical clip of claim 5, wherein the ratio of the length of the legs to the total length of the clip ranges from about 0.36 to about 0.33.

7. The surgical clip of claim 1, wherein the interior surface of the first back portion includes an elongated ridge extending along the linear orientation thereof and the interior surface of the second back portion includes a recess for receiving the elongated ridge of the first back portion upon movement of the clip legs from the open to the closed position.

8. The surgical clip of claim 1, wherein the interior surface of the second clip leg includes an interlock protrusion and the interior surface of the first leg includes a recess for receiving the interlock protrusion of the second leg upon movement of the first and second legs from the open position to the closed position.

9. The surgical clip of claim 1, wherein the clip is fabricated from a material selected from the group consisting of stainless steel and titanium.

10. The surgical clip of claim 1, wherein the first and second back portions are curved.

11. A surgical clip which comprises:
a) a bail portion having first and second arcuate back portions joined to each other at an apex, each of the first and second back portions having an exterior surface and an interior surface, wherein the exterior surface of the second back portion includes an elongated ridge extending along the orientation thereof, and wherein the apex is characterized by an angle of no greater than about 100°, the arcuate back portions having no curve with a radius of curvature less than six times that of the apex; and
b) first and second rectilinear legs, each leg having a distal free end and an interior tissue contacting surface and an exterior surface for receiving a compressive force, each leg being joined to a respective one of the first and second back portions and moveable in response to an externally applied compressive force from an initial spaced apart, open configuration to a closed configuration, wherein the first and second legs are initially substantially parallel to each other and remain substantially parallel to each other during the process of moving from the open configuration to the closed configuration.

12. The surgical clip of claim 11, wherein the clip is characterized a total length defined by the distance between the apex and the free ends of the first and second legs, and a width defined by the distance between the exterior surfaces of the first and second legs, and the ratio of the width to the length ranges from about 0.68 to about 0.64.

13. The surgical clip of claim 12, wherein the first and second legs are of equal length.

14. The surgical clip of claim 13 wherein the ratio off the length of the legs to the total length of the clip ranges from about 0.36 to about 0.33.

15. The surgical clip of claim 11, wherein the interior surface of the first back portion includes an elongated ridge extending along the linear orientation thereof and the interior surface of the second back portion includes a recess for receiving the elongated ridge of the first back portion upon movement of the clip legs from the open to the closed position.

16. The surgical clip of claim 11, wherein the interior surface of the second clip leg includes an interlock protrusion and the interior surface of the first leg includes a recess for receiving the interlock protrusion of the second leg upon movement of the first and second legs from the open position to the closed position.

17. The surgical clip of claim 11, wherein the clip is fabricated from a material selected from the group consisting of stainless steel and titanium.

18. In combination with a surgical clip applying apparatus having a pair of opposing jaws for compressing the legs of a surgical clip from an open position to a closed position, at least one surgical clap which comprises:
   a) a bail portion having first and second curved back portions joined to each other at an apex, each of the first and second back portions having an exterior surface and an interior surface, wherein the exterior surface of the second back portion includes an elongated ridge extending along the arcuate orientation thereof, and wherein the apex is characterized by an angle of no greater than about 100°; and
   b) first and second rectilinear legs, each leg having a distal free end and an interior tissue contacting surface and an exterior surface for receiving a compressive force, each leg being joined to a respective one of the first and second back portions and moveable in response to an externally applied compressive force from said opposing jaws from an initial spaced apart open configuration to a closed configuration, wherein the first and second legs are initially substantially parallel to each other and remain substantially parallel to each other during the process of moving from the open configuration to the closed configuration.

19. The combination of claim 18, wherein the at least one surgical clip comprises a plurality of surgical clips arrayed in a row extending along a longitudinal axis of the instrument in a clip feeding and storage track, and further wherein the clips are positioned such that the legs of one clip contact the bail portion of the preceding clip.

20. The combination of claim 18, wherein the clip is characterized a total length defined by the distance between the apex and the free ends of the first and second legs, and a width defined by the distance between the exterior surfaces of the first and second legs, and the ratio of the width to the length ranges from about 0.68 to about 0.64, and wherein the ratio of the length of the legs to the total length of the clip ranges from about 0.36 to about 0.33.

* * * * *